US006814864B1

United States Patent
Favre et al.

(10) Patent No.: US 6,814,864 B1
(45) Date of Patent: Nov. 9, 2004

(54) EXTRA-CORPOREAL BLOOD PURIFICATION DEVICE

(75) Inventors: Olivier Favre, Geneva (CH); Francesco Di Lella, Geneva (CH)

(73) Assignee: Infomed SA, Geneva (CH)

( * ) Notice: Subject to any disclaimer, the term of this patent is extended or adjusted under 35 U.S.C. 154(b) by 60 days.

(21) Appl. No.: 10/111,771

(22) PCT Filed: Oct. 26, 2000

(86) PCT No.: PCT/CH00/00573
§ 371 (c)(1),
(2), (4) Date: Apr. 29, 2002

(87) PCT Pub. No.: WO01/32238
PCT Pub. Date: May 10, 2001

(30) Foreign Application Priority Data

Oct. 29, 1999 (EP) ............................................. 99810984

(51) Int. Cl.$^7$ ......................... B01D 61/28; B01D 61/32; B01D 61/34
(52) U.S. Cl. ...................... 210/321.65; 210/85; 210/87; 210/90; 210/97; 210/102; 210/106; 210/134; 210/142; 210/143; 210/929
(58) Field of Search ............................. 210/85, 87, 90, 210/97, 102, 106, 134, 142, 143, 321.65, 929; 604/4.01, 6.09, 6.11

(56) References Cited

U.S. PATENT DOCUMENTS

| 5,714,060 | A | | 2/1998 | Kenley et al. | ............... | 210/194 |
| 5,762,805 | A | * | 6/1998 | Truitt et al. | ................. | 210/645 |
| 6,303,036 | B1 | * | 10/2001 | Collins et al. | .............. | 210/646 |
| 6,406,631 | B1 | * | 6/2002 | Collins et al. | .............. | 210/646 |
| 6,471,872 | B2 | * | 10/2002 | Kitaevich et al. | ........... | 210/739 |

FOREIGN PATENT DOCUMENTS

| EP | 0 235 591 A1 | 9/1987 |
| EP | 0 722 744 A | 7/1996 |
| EP | 0834329 | 4/1998 |
| WO | 83/04373 | 12/1983 |
| WO | WO 98/50091 | 11/1998 |

OTHER PUBLICATIONS

English Translation of WO 98/50091 A1.*

* cited by examiner

Primary Examiner—John Kim
(74) Attorney, Agent, or Firm—Young & Thompson

(57) ABSTRACT

An extra-corporeal blood purification device includes a blood filter, and elements for measuring at least one parameter affected by filter resistance to liquid flow, elements for determining at least a threshold value of the parameter, elements for comparing the parameter with the threshold value, exchange control elements for calculating the distribution between the respective flow rates through connecting ducts, capable of reducing the difference between the value of the measured parameter and the threshold value.

19 Claims, 5 Drawing Sheets

EXTRA-CORPOREAL BLOOD PURIFICATION DEVICE

BACKGROUND OF the INVENTION

The present invention relates to a device for the purification of blood comprising a blood extraction conduit, a blood return conduit, blood filtration means located between the extraction conduit and the return conduit, means to circulate the blood, an evacuation conduit for the liquid from said filtration means called the ultra-filtrate, means to circulate the ultra-filtrate in said evacuation conduit, a source of substitution solution, a connection conduit between this source and said blood extraction conduit, pre-dilution control means to circulate the substitution solution, means for measuring at least one parameter influenced by the resistance of the filtration means to the flow of the liquid, and a computation unit.

The extra-corporeal purification has for its object on the one hand to clean the blood of patients by withdrawing undesirable elements and on the other hand controlling the weight of the patients. The invention is applicable most particularly to hemo-filtration which is distinguished from dialysis by the fact that the purification takes place by convection rather than by diffusion through a semi-permeable membrane. In the two cases, the operator is required to intervene during the sessions, in particular to avoid coagulation in the extra-corporeal circulation conduit, which takes place particularly at the filter.

The coagulation of extra-corporeal circulation during hemo-filtration is conventionally reduced by using anticoagulants (heparin, liquemin) and by proceeding at regular intervals to rinse the circuit and change the filters.

Although often well tolerated by patients at conventional dosages, the use of anticoagulants is contraindicated in certain cases, for example for patients having substantial lesions.

As to rinsing, this is an operation which consists in causing the physiological liquid to circulate instantaneously in the filter in place of the blood. This takes place by obstructing the blood extraction conduit with a clamp, connecting a pouch of physiological liquid to the blood extraction conduit, making sure that a sufficient quantity of physiological liquid has flowed, conventionally 100 to 300 ml. This quantity is considered as suitable to clean the filter. The previous flow conditions are then reestablished to continue the treatment. This sequence of operations takes a long time and can lead to handling errors. Moreover, it interrupts the treatment and the operator must take account of the surplus of liquid injected into the patient when calculating the hydric balance of the patient.

In the case in which a change of the filter is necessary, it is necessary to return his blood to the patient, rinse the new filter, then continue the treatment. This operation is long and costly and should therefore be avoided whenever possible.

It should also be noted that, to the phenomenon of coagulation, there is also that of clogging, which is a deposit of molecules on the extra-corporeal circulation surfaces and particularly the filter walls. This clogging also reduces the capacity for blood purification and is eliminated in the same way as coagulated deposits. In what follows of this specification there will be used indiscriminately the terms coagulation or clogging to designate these two phenomena.

DESCRIPTION OF the RELATED ART

It was proposed in WO 83/04373 to provide an apparatus for automatically carrying out rinsing by actuating electro-mechanical clamps at predetermined time intervals, by the operator. EP 0 235 591 proposes adding a clamp which permits varying the pressure in the filter so as to increase the rinsing effect. The drawback of these two solutions resides in the fact that the rinsing is decided by the user who has only an approximate idea of the speed of coagulation of the system. As a result, either the rinsing is too frequent, which decreases the effectiveness of the treatment by repeated interruptions of the treatment, or else it is not frequent enough, leading to coagulation by insufficient rinsing.

WO 98/50091 describes a process for controlling an extra-corporeal blood purification device, this latter comprising a blood extraction conduit, a blood return conduit, blood filtration means, means to circulate the blood, an evacuation conduit for ultra-filtrate from said filtration means, means to cause the ultra-filtrate to circulate, a source of substitution solution, a connection conduit between this source and the blood extraction conduit, a means to cause the substitution solution to circulate in this connecting conduit. This device also comprises a computation unit and measuring means which can permit determining at least one parameter influenced by the resistance of the filtration means to the flow of liquid. The process disclosed in this document permits such an apparatus moreover to compare the measured parameters with threshold values, control means applying new reference values to reduce the difference between the value of the measured parameter and the threshold value. This process is however limited to the good operation of the apparatus as to its principal functions, which is to say to regulate the circulation of the fluid in the two circuits of the apparatus and particularly to balance the extracted and substituted masses. No reference is made to a solution to avoid or actively remove coagulation of the blood by using the process or the device proposed in this document.

It is to be noted that the exchange volume, to which corresponds an exchange flow rate, is defined as being the volume of liquid taking part in purification of the blood withdrawn from this latter in the course of the session. If there is no loss, particularly by pre-dilution, this volume corresponds to that of the ultra-filtrate. This is the quantum which, in hemo-filtration, determines the degree of purification of the blood in the course of the session, which can also be defined as being the quantity of impurities withdrawn from the blood.

None of the systems described above is really satisfactory, because they are not adaptable to variations in the operating parameters which can arise during the treatment. Moreover, the patients are regularly purified in an insufficient manner because the prescribed volumes are calculated by assuming that all the substitution liquid is injected with post-dilution, the values not being corrected to take account of the proportion of this liquid introduced by pre-dilution.

The physical parameters which can have an influence on the coagulation of the system are numerous. There can be particularly cited the material and the surface of the filter, the blood composition and flow rate, the dosage of anticoagulant prescribed and the desired exchange flow rate. These parameters can vary in the course of the treatment in important ways and at short intervals. It is thus impossible for the user to control the condition of the system so as to avoid systematically its coagulation. This is all the more true when the duration of the treatment can be several days and the exchange flow rates are great, for example 12 liters per hour.

SUMMARY OF the INVENTION

The object of the present invention is to overcome at least in part the above-mentioned drawbacks.

To this end, this invention has for its object an extra-corporeal blood purification device of the type mentioned above.

An essential advantage of this invention resides in the fact that this device does not require the intervention of the user during the treatment.

The device according to the invention permits minimizing the substitution solution consumed and adapting the exchange volume so as to observe, to the extent possible, all the standards required by the user.

BRIEF DESCRIPTION OF the DRAWINGS

The invention will be better understood with the help of the following description and the accompanying drawings, which show schematically and by way of example one embodiment of the device of this invention.

DESCRIPTION OF the PREFERRED EMBODIMENTS

Figure 1:
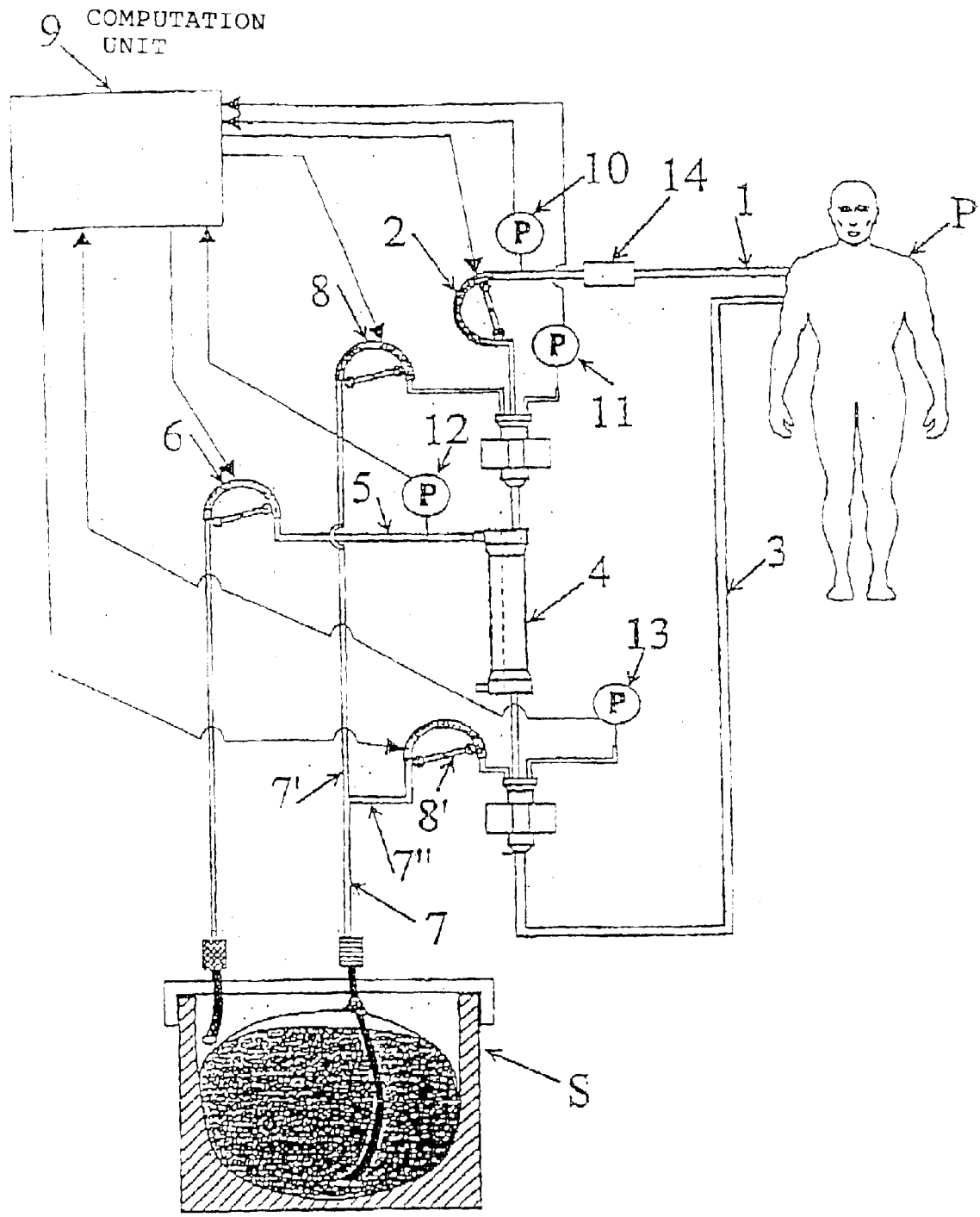
FIG. 1 is a schematic of this embodiment.

The invention has means for the extra-corporeal circulation of blood, comprised by an extraction conduit 1, a pump 2 to extract the blood from the body of the patient P and the return conduit 3 to return the purified blood to the body of the patient P. A filter 4 permits carrying out purification of the blood, thanks to an evacuation conduit 5 for the polluted solution, called ultra-filtrate, having a flow control means 6.

A substitution solution conduit 7 connects a reservoir S of substitution solution to the extra-corporeal circulation circuit 1, 3. This conduit is divided into two conduits 7' and 7", the first 7' connecting the source S of substitution liquid to the blood extraction conduit 1 upstream of the filter 4, the second 7" connecting this source S to the return conduit 3, downstream of the filter 4. The flow rate of pre-dilution liquid through the conduit 7' is controlled by a peristaltic pump 8. The flow rate of post-dilution liquid through the conduit 7" is controlled by a peristaltic pump 8'. The pre-dilution liquid can as desired be injected upstream or downstream of the pump 2 for extraction of the blood.

Computation means 9 serve to determine the proportion of the flow rate of the pre-dilution liquid and that of the post-dilution liquid. Detectors 10, 11, 12 and 13, of pressure or flow rate, are disposed at different places in the blood circulation circuit 1, 3 and in the evacuation conduit 5 for the ultra-filtrate. These detectors 10, 13 are connected to the computation unit 9 to supply it with the parameters necessary for the determination of the respective quantities of the flow rates of substitution liquid to be sent to the conduits 7' and 7" and corresponding to the computed values of pre-dilution and post-dilution.

The usual components of the extra-corporeal purification devices which do not take part directly in the field of the present invention are not shown. These are particularly the air bubble detectors, the closure clamp for the blood return line 3, the blood loss detector, the re-heater for the blood or for the substitution liquid, and the means for measuring the flowing masses.

The control means of the flow rates are typically peristaltic pumps or clamps controlled by the computation unit 9.

The invention is also applicable to systems for extra-corporeal circulation with a single needle and to dialysis apparatus including or not the preparation of the solutions, as well as to combined methods such as hemodiafiltration.

The progress of coagulation of the filter can be followed by measuring the pressure difference of the blood between the inlet and the outlet of the filter 4, the trans-filter pressure, computed from the difference of the values supplied by the detectors 11 and 13, and/or by the transmembrane pressure $P_{tm}$ usually defined as being the pressure difference between the pressure $P_{12}$ of the ultra-filtrate conduit measured by the detector 12 and the mean pressure $P_{mean}$ computed from the values of the detectors 11 and 13, namely $P_{tm}=((P_{11}+P_{13})/2)-P_{12}$.

To achieve the treatment object by avoiding coagulation of the filter 4, a system according to the invention adapts the flow rates of substitution liquid in the conduits 7', 7" so as to maintain the value of the parameters influenced by this phenomenon within normal operating values and adapts the exchange volume, and as a result the ultra-filtrate flow rate, by taking account of the substitution liquid flow rate which effectively flows in the pre-dilution conduit 7, so as to correct its value by deducing the portion of the substitution liquid that has not participated in purification. Moreover, the system minimizes the volume of substitution liquid which flows in the pre-dilution conduit 7', so as to avoid wasting this substitution liquid and to achieve a better degree of purification in the given time.

Figure 2:
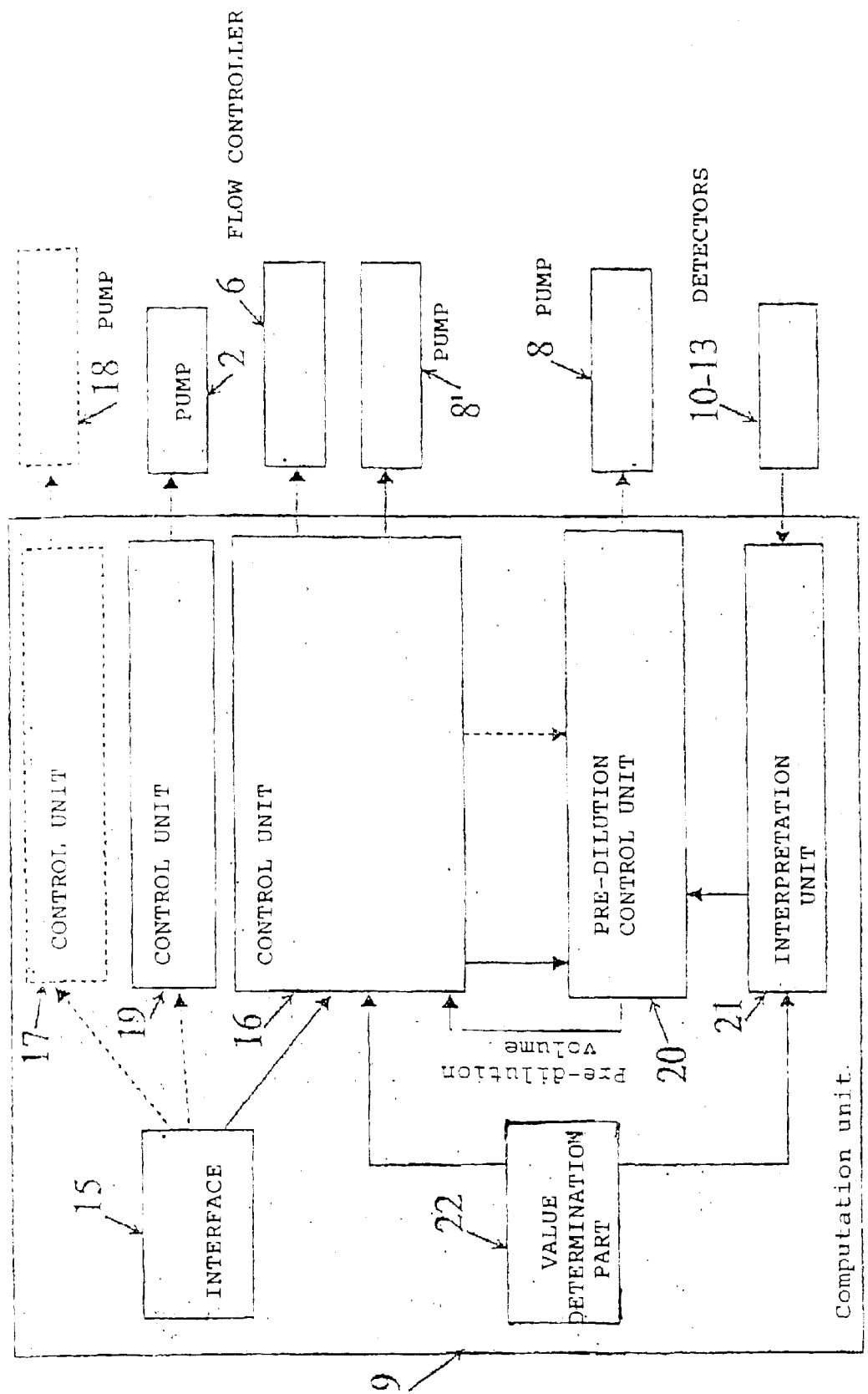
FIG. 2 is a block schematic of the computation means 9.

The block diagram of the computation unit 9 shown in FIG. 2 comprises an interface 15 with the help of which the operator can introduce the specifications relating to the treatment. This interface 15 is connected to an exchange control unit 16 which comprises a computation program to control the ultra-filtrate pump 6 and the post-dilution pump 8 according to indications from, among others, the interface 15, as well as data and/or computation rules which can be contained in a memory (not shown).

The interface 15 moreover can be connected to a control unit 17 of an anticoagulant distribution station 18, as well as a control unit 19 for the blood extraction pump 2 which acts as a function of the indications of the operator or of the predefined flow optimization rules.

The computer 9 also comprises a control unit 20 for pre-dilution, connected on the one hand to the control unit 16 for the value of exchange and to an interpretation unit 21 for the measurements carried out by the detectors 10–13, and on the other hand to the pre-dilution pump 8. The pre-dilution control unit 20 establishes the initial value of the quantity of pre-dilution as a function of instructions received from the control unit 16 for the exchange value or for rules or values previously recorded in the unit 20. This latter increases or decreases the flow rate of the pre-dilution pump 8 as a function of the interpretation of the values measured by the detectors 10–13, which itself supplies the interpretation unit 21. As a modification, the control unit 16 of the exchange value supplies directly to the pre-dilution control unit a reference value to be applied to the pre-dilution pump 8, said value being established on the basis of the computation rules recorded in the computation means 9. An example of such a rule consists in maintaining the pre-dilution reference at zero for an ultra-filtrate flow rate less than a predetermined value, then increasing said pre-dilution flow rate according to a curve proportionate to the increase of the ultra-filtrate above said predetermined value.

Figure 3:
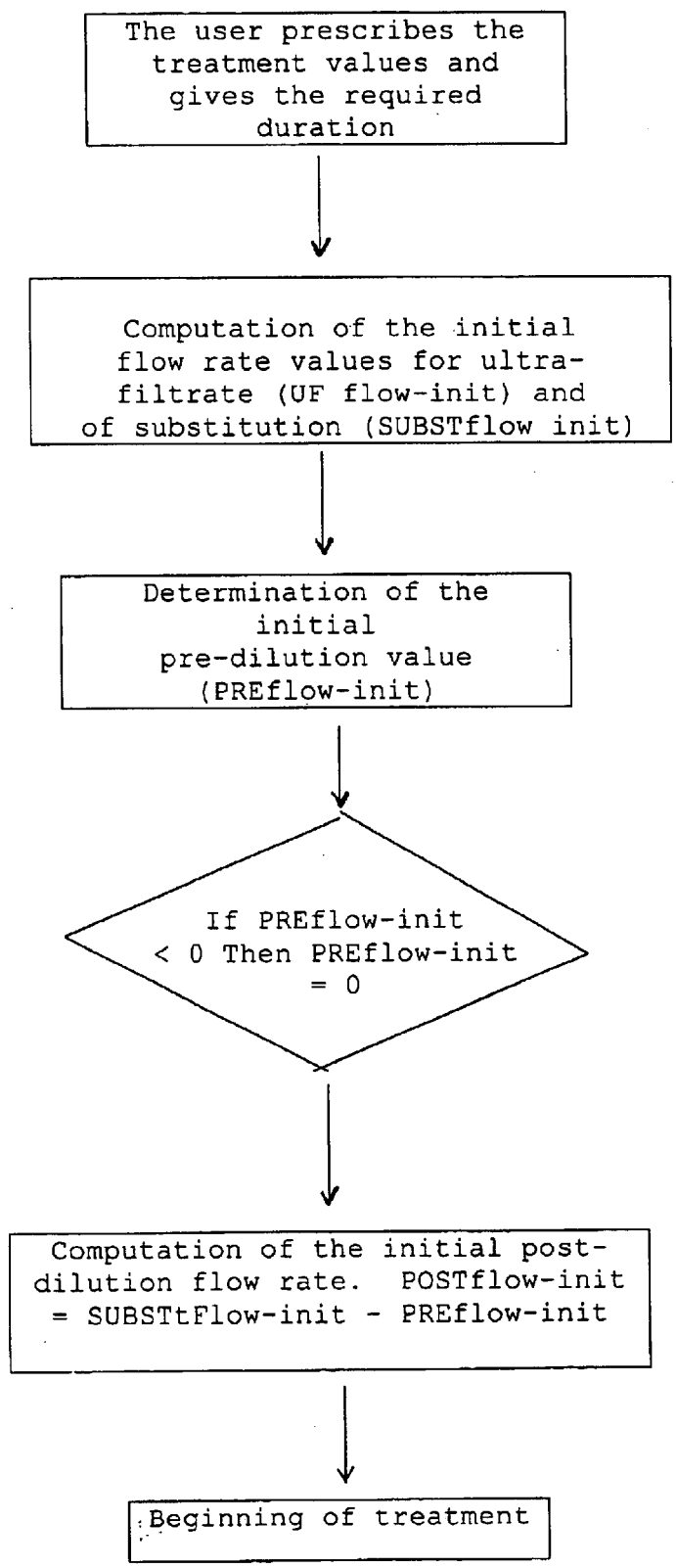
FIG. 3 shows the sequence of operations for starting the device.

As described in the sequence of operations relating to the startup shown in FIG. 3, of the extra-corporeal circulation device, the operator adapts, prior to the treatment properly so-called, the exchange value and the duration of treatment, the initial ultra-filtrate flow rate being computed by carrying out the division of the volume by the prescribed duration. The substitution liquid flow rate is adapted to that of the ultra-filtrate, corrected by values (desired weight loss, external supply and loss) necessary to maintain or adapt the weight of the patient as required by the operator and divided in two according to an initial ratio between post-dilution and pre-dilution, determined on statistical bases.

Figure 4:
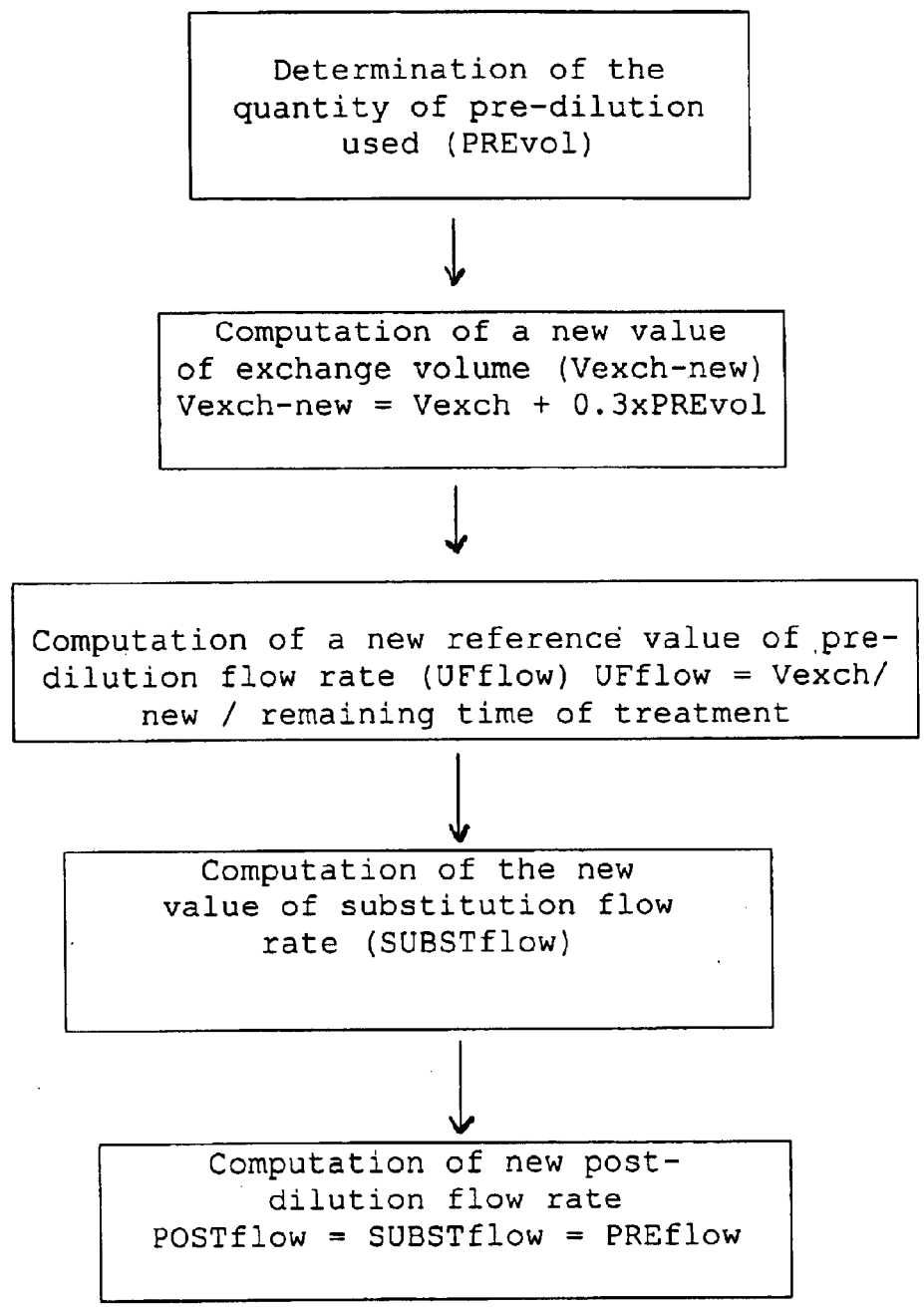
FIG. 4 shows the sequence of operations for adjusting the flow rates of the ultra-filtrate and of the substitution liquid, including the computation of the new exchange volume made necessary by the use of pre-dilution.
Figure 5:
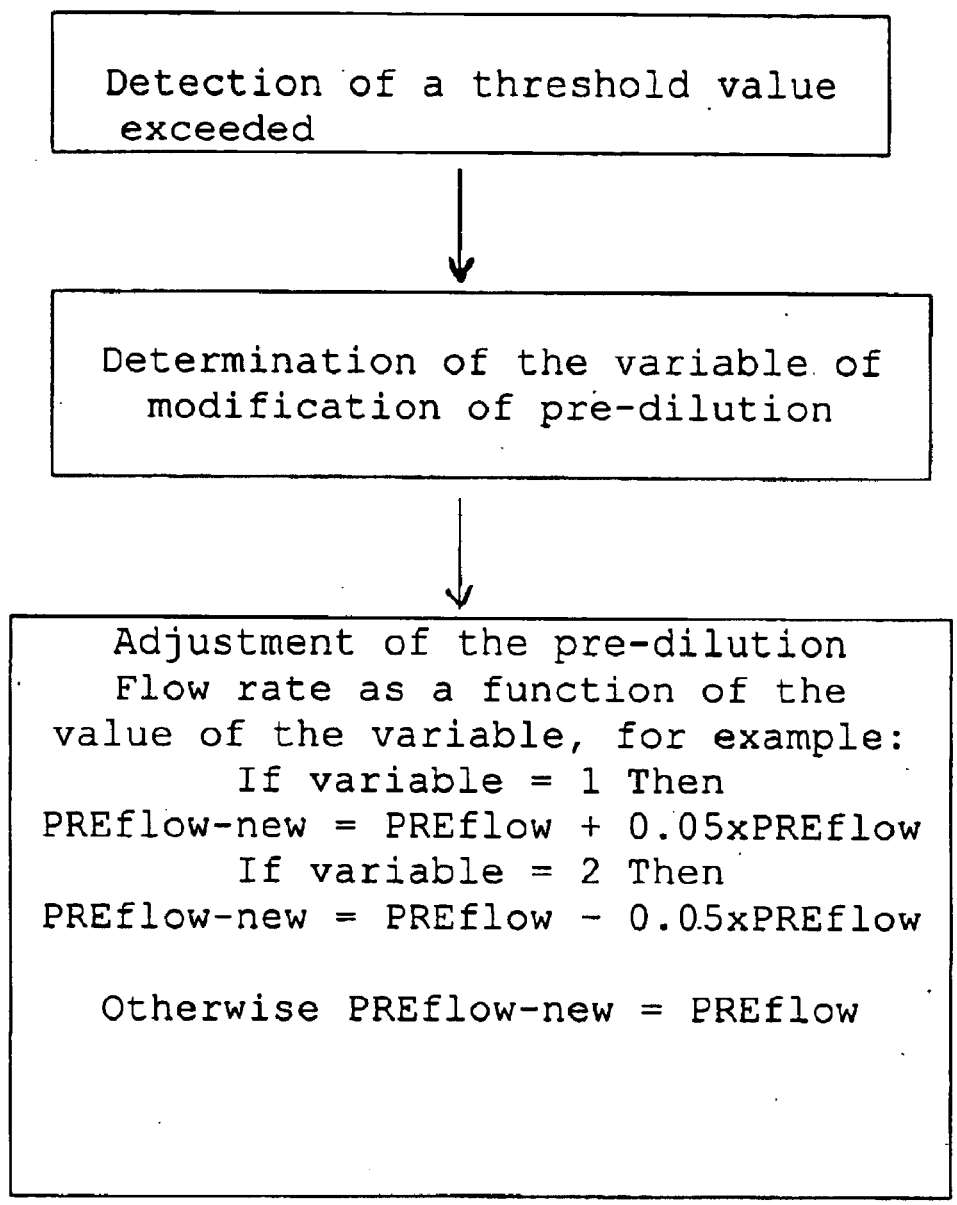
FIG. 5 shows the sequence of operations for adjusting the quantity of pre-dilution.

As shown in FIG. 4, during the treatment, the quantity of substitution liquid that flows in the pre-dilution conduit 7' is measured or computed, its value being used to determine a new exchange volume corresponding to a degree of purification identical to that determined by the volume initially prescribed. The flow rate of ultra-filtrate 5 is then adapted so as to correspond to this new exchange volume, and if possible to achieve the objectives of purification and weight variation of the patient during the prescribed duration of treatment.

The physical limits of the material are recorded in the computation unit 9, such as for example the limits of the control means of the flow rate and the limits of the linear ratio between the drop in the degree of purification and the pre-dilution value which will appear by increasing the liquid flow rate in the pre-dilution conduit 7'. The point beyond which the degree of purification is considered as insufficient with respect to the substitution liquid consumed, is determined by the variables of blood and filter taking part in coagulation. It can be determined experimentally and recorded in the computation unit 9 or measured continuously, for example by dosage with urea and its variation in the ultra-filtrate 5. To determine whether a physical limit is theoretically exceeded, the admissible limit value of the corresponding parameter is memorized. If an admissible limit value is exceeded, the computation unit assigns the value of the parameter to its limit value and prolongs the duration of treatment beyond the duration required to permit reaching the desired objectives.

Given that the higher the blood flow rate extracted from the patient, the better are the filtration conditions of the device, it can be advantageous to add a flow rate detector 14 in the extraction conduit 1 to optimize this flow rate. To this end, the control unit 19 of the blood extraction pump 2 periodically increases the speed of this pump 2 until the increase of the blood flow rate extracted no longer linearly increases with the increase of the speed of the pump 2, thereby indicating that the maximum admissible flow rate of the vascular access of the patient has been exceeded. At this time, the control unit 19 of the blood pump 2 decreases the speed of this pump 2 so as to reach the last known value so as to be within the linear range.

This control can be carried out in a repeated manner during the treatment so as to maintain the blood flow rate under conditions optimum for filtration. The flow rate detector 14 will preferably also be used to determine precisely the blood flow rate.

The anticoagulant flow rate can be zero or not, supplied by an auxiliary pressure syringe or by a pump 18 controlled by the computation unit 9.

To determine the flow rates in a manner according to the invention, the computation unit 9 can have the arrangement shown in FIG. 2, the invention not being limited to this example.

Data on the configuration of the apparatus are initially recorded, generally at a time other than a therapeutic session, in the computation unit 9. These data can comprise the definition of the standard treatments, particularly the name of the treatment, the exchange volume, the required duration and the tubing and filters used, and the addition and loss of external liquids to the apparatus, particularly the type of addition or loss, the flow rate by default and the weight to be achieved. These values can be modified during the treatment, the apparatus then taking account of the new values.

At the beginning of a session, the operator indicates the prescribed treatment values, for example the hydric balance of the patient, the desired loss of weight or profusion. If necessary, he modifies the initially defined values which appear by default. This startup of the purification apparatus is shown by the schematic diagram of FIG. 3. The blood flow rate is defined according to one of the methods described above. The computation unit 9 thus determines the ultra-filtrate flow rate and the initial flow rate of the substitution liquid, the quantity of pre-dilution being either zero or computed on the basis of previously defined rules recorded in the apparatus. Ideally, the initial pre-dilution flow rate will be near the normal value of operation desired. The treatment begins and the trans-filter and/or trans-membrane pressures are measured so as to determine in several seconds their normal operating values which correspond to a stable condition of the device satisfying in its operation according to the predetermined rules.

During the treatment, the flow rates of the different pumps 2, 6, 8 and 8' are adjusted automatically, either at regular time intervals, or on the basis of a predetermined event such as for example an abrupt increase of pressure, by measuring the pressure values 10–13 comparing these values to those considered as being normal operating values. There can thus be determined a variable with three conditions which define particularly whether it is necessary to reduce, increase or maintain the quantity of pre-dilution.

The quantity of pre-dilution is then adjusted as a function of the value of the variable with three conditions, then the necessary increase volume is computed, the flow rate of ultra-filtrate being adapted to this new value.

The rules permitting determining said three-condition variable can be defined in several ways, for example, the quantity of pre-dilution at each cycle of adjustment can be decreased as long as the pressures do not increase by more than 10% relative to the value predetermined as being the operating value, or such that the pressures do not have an increase of more than 5% per 30 seconds. Similarly, the criteria for maintaining and increasing the quantity of pre-dilution can be determined. The reference values of the pumps 6 and 8' are then adapted by taking account of the new reference value for pre-dilution.

A variant consists in giving the pressure measurements 10–13 to the unit 16 which then computes the references for the pumps 6, 8 and 8' taking account of the measurements and. The computation rules previously recorded.

It is also possible to use other variables than pressures. The measurements of ultra-filtrate flow rate for speed pumps or predetermined clamp openings are also indicators of the level of clogging of the filter.

Because the parameters which influence the normal pressure levels change in the course of the treatment, it will be useful to modify them in the course of the treatment. A possible way is to consider any level which is stable for at least five minutes, as the new normal operating level.

The adaptation of pre-dilution may not suffice sufficiently to clean the filter 4. Thus, if this latter clogs, which is for example determined by a trans-membrane pressure value greater than a previously defined limit, or by a rapid increase of said pressure, cleaning is carried out by stopping the blood extraction pump 2, the ultra-filtrate pump 6 and the post-dilution pump 8' for a time or for a volume or predetermined mass of restitution liquid, and by actuating the pre-dilution pump 8 so as to cause the physiological dissolution to circulate in the place of the blood and thereby to rinse the filter 4. The solution mass injected into the patient during rinsing carried out in this way is then deduced during the rest of the treatment.

The benefit of the invention is threefold: reduction of the quantity of costly sterile substitution medical solution used, avoidance of clogging of the extra-corporeal circulation without the required addition of anticoagulants, and automatic adjustment of the exchange volume to obtain the desired degree of purification.

What is claimed is:

1. Device for the extra-corporeal purification of blood, comprising:

a blood extraction conduit (1), a blood return conduit (3), blood filtration means (4) located between the extraction conduit (1) and the return conduit (3), means (2) to cause the blood to circulate, an ultra-filtrate evacuation conduit (5) from said filtration means (4), means (6) to cause the ultra-filtrate to flow in said evacuation conduit (5), a source (S) of substitution solution, a connecting conduit (7') between said source (S) and the blood extraction conduit (1), pre-dilution control means (8) to cause the substitution solution to flow in this connecting conduit (7'), measuring means (10, 11, 12, 13) for at least one parameter influenced by the resistance of the filtration means (4) to the flow of liquid, and a computation unit (9), the computation unit (9) comprising a pre-dilution control unit (20) which pre-dilution control unit is connected on the one hand to an interpretation unit (21) of at least one measuring means (10, 11, 12, 13) of a parameter influenced by the resistance of the filtration means (4) to the flow of the liquid, and on the other hand to the pre-dilution control means (8), and which computation unit controls the pre-dilution control means (8) as a function of the values received from the interpretation unit (21) so as to maintain or reduce the resistance of the filtration means (4) to the flow of the liquid.

2. Device according to claim 1, characterized by the fact that the measuring means (10, 11, 12, 13) permit computing the trans-filter pressure.

3. Device according to claim 1, characterized by the fact that the measuring means (10, 11, 12, 13) permit computing the trans-membrane pressure.

4. Device according to claim 1, characterized by the fact that the measuring means (10, 11, 12, 13) permit computing the ultra-filtrate flow rate through the evacuation conduit (5).

5. Device according to claim 1, characterized by the fact that the pre-dilution control unit (20) controls the dilution control means (8) according to a curve proportional to the desired ultra-filtrate flow rate.

6. Device according to claim 5, characterized by the fact that the pre-dilution control unit (20) controls the pre-dilution control means (8) only in the linear portion of the ratio between the degree of purification and the flow rate of the substitution solution.

7. Device according to claim 1, characterized by the fact that the computation unit (9) prolongs the duration of the treatment until the desired purification degree is obtained.

8. Device according to claim 1, characterized by the fact that the computation unit (9) carries out a cleaning of the filtration means (4) by controlling the pre-dilution control means (8), the means (2) to circulate the blood and the means (6) to circulate the ultra-filtrate, so as to cause the rinsing liquid to circulate in place of the blood.

9. Device for the extra-corporeal purification of blood, comprising:

a blood extraction conduit (1);

a blood return conduit (3);

a blood filtration means (4) located between the extraction conduit (1) and the return conduit (3);

a means (2) to cause the blood to circulate;

an ultra-filtrate evacuation conduit (5) from said filtration means (4);

a means (6) to cause the ultra-filtrate to flow in said evacuation conduit (5);

a source (S) of substitution solution;

two connecting conduits (7', 7") between said source (S) and said blood extraction conduit (1), and between source (S) and said blood return conduit (3);

a means (8, 8') to cause the substitution solution to flow in each of said connecting conduits (7', 7");

a measuring means (10–13) of at least one of the parameters influenced by the resistance of the filtration means (4) to the flow of the liquid;

a means (22) to determine at least one threshold value of said parameter;

a means (21) to compare said parameter with said threshold value; and an exchange control means (16) to compute the distribution of the respective flow rates through said connecting conduits (7', 7"), said exchange control means adapted to automatically reduce the difference between the value of said measured parameter and said threshold value.

10. Device according to claim 9, wherein, said measuring means (10–13) of at least one of said parameters influenced by the resistance of the filtration means (4) to the flow of the liquid, measures at least one value adapted to determine the trans-membrane pressure or the trans-filter pressure of said filtration means (4).

11. Device according to claim 9, wherein, said measuring means (10–13) of at least one of the parameters influenced by the resistance of the filtration means (4) to the flow of the liquid, measures the ultra-filtrate flow rate through the evacuation conduit (5).

12. Device according to claim 9, wherein, said means (22) to determine at least one threshold value of said parameter, computes this threshold value on the basis of said measured parameters or of the change with time of at least one of said parameters.

13. Device according to claim 9, further comprising:

a means (21) to detect when at least one threshold value is exceeded, and wherein, said exchange control means (16) is programmed to stop said means (2, 6, 8') which causes circulation of the blood, the ultra-filtrate and the substitution liquid in said connection conduit (7") connecting said substitution liquid source (S) to said return conduit (3), while said substitution liquid circulation means (8) and said extraction conduit (1) are actuated, until a volume, a mass of substitution liquid, or a predetermined duration, have occurred.

14. Device according to claim 9, further comprising:

a means (21) to detect when at least one threshold value is exceeded, and wherein, said pre-dilution control means (20) is programmed to modify the reference value of the flow rate of the fluid circulation means (8) between said substitution liquid source (S) and said blood extraction conduit (1), consecutively to the threshold value being exceeded.

15. Device according to claim 9, wherein, said exchange control means (16) are programmed to carry out an exchange volume compensation established as a function of the volume or the mass of substitution liquid injected into the conduit (7') connecting the substitution liquid source (S) to the blood extraction conduit (1).

16. Device according to claim 9, wherein, the physical limits of flow rate of the substitution liquid circulation means and of the ultra-filtrate (6, 8, 8') are recorded in said exchange control means (16) and pre-dilution control means (20) which are programmed to prolong the duration of treatment if the prescribed treatment values cannot be reached during the required time, taking account of said physical limits of recorded flow rates.

17. Device according to claim 9, wherein, the exchange control means (16) are programmed to compute the reference values of flow rate for the pre-dilution control means (20), on the basis of recorded rules.

18. Device according to claim 9, wherein, said blood extraction conduit (1) comprises a flow rate detector (14) connected to the computation unit (9), which computation unit comprises a means (19) to determine the maximum flow rate tolerated by the patient-vascular access combination, by increasing the speed of the blood extraction pump (2) and by comparing the linearity of the increase of flow rate with the increase of the speed of said pump (2), and by decreasing the speed of said pump (2) when the flow rate/speed ratio is no longer linear, to return the speed of the pump (2) to the last value comprised within the linear range.

19. Device for the extra-corporeal purification of blood, comprising:

a blood extraction conduit (1);

a blood return conduit (3);

a blood filtrator (4) located between the extraction conduit (1) and the return conduit (3);

a blood circulation unit to cause the blood to circulate;

an ultra-filtrate evacuation conduit (5) connected from said filtrator (4);

a flow controller (6) to cause the ultra-filtrate to flow in said evacuation conduit (5);

a source (S) of substitution solution;

a connecting conduit (7') between said source (S) and the blood extraction conduit (1);

pre-dilution controller (8) for causing the substitution solution to flow in the connecting conduit (7');

measuring elements (10, 11, 12, 13) for at least one parameter influenced by the resistance of the filtrator (4) to the flow of liquid; and a computation unit (9) comprising a pre-dilution control unit (20) which is connected i) to an interpretation unit (21) of at least one measuring elements (10, 11, 12, 13) of a parameter influenced by the resistance of the filtration means (4) to the flow of the liquid, and ii) to the pre-dilution controller (8), and an exchange control unit (16) connected to the flow controller (6), which exchange control unit adapts the value of ultra-filtrate flow rate as a function of the flow rate of the substitution solution which has effectively flowed out, which computation unit controls the pre-dilution controller (8) as a function of the values received from the interpretation unit (21) so as to maintain or reduce the resistance of the filtrator (4) to the flow of the liquid.

* * * * *